US009717807B2

(12) United States Patent
Kim et al.

(10) Patent No.: US 9,717,807 B2
(45) Date of Patent: Aug. 1, 2017

(54) CT CONTRAST MEDIUM FOR DETECTING THROMBUS, COMPRISING FIBRIN-TARGETED PEPTIDE SEQUENCE-CONJUGATED GLYCOL CHITOSAN-GOLD NANOPARTICLES

(71) Applicants: DONGGUK UNIVERSITY INDUSTRY-ACADEMIC COOPERATION FOUNDATION, Seoul (KR); SNU R&DB FOUNDATION, Seoul (KR); KOREA INSTITUTE OF SCIENCE AND TECHNOLOGY, Seoul (KR)

(72) Inventors: Dong Eog Kim, Gyeonggi-do (KR); Jeong Yeon Kim, Gyeonggi-do (KR); In Cheol Sun, Seoul (KR); Sung Kyung Park, Seoul (KR); Cheol Hee Ahn, Seoul (KR); Kwang Meyung Kim, Seoul (KR)

(73) Assignees: Dongguk University Industry-Academic Cooperation Foundation (KR); SNU R & DB Foundation (KR); Korea Institute of Science and Technology (KR)

( * ) Notice: Subject to any disclaimer, the term of this patent is extended or adjusted under 35 U.S.C. 154(b) by 306 days.

(21) Appl. No.: 14/402,214

(22) PCT Filed: May 13, 2013

(86) PCT No.: PCT/KR2013/004213
§ 371 (c)(1),
(2) Date: Nov. 19, 2014

(87) PCT Pub. No.: WO2013/176432
PCT Pub. Date: Nov. 28, 2013

(65) Prior Publication Data
US 2015/0139912 A1 May 21, 2015

(30) Foreign Application Priority Data
May 23, 2012 (KR) ........................ 10-2012-0054614

(51) Int. Cl.
*A61K 51/00* (2006.01)
*A61M 36/14* (2006.01)
*A61K 49/04* (2006.01)
*B82Y 5/00* (2011.01)
*G06T 11/00* (2006.01)

(52) U.S. Cl.
CPC .......... *A61K 49/04* (2013.01); *A61K 49/0428* (2013.01); *B82Y 5/00* (2013.01); *G06T 11/003* (2013.01)

(58) Field of Classification Search
CPC .... A61K 49/00; A61K 38/00; A61K 2123/00; A61K 2121/00; A61K 49/04; A61K 49/0428; B82Y 5/00; G06T 11/003
USPC ........ 424/1.11, 1.65, 1.69, 9.1, 9.2, 9.3, 9.4, 424/9.5, 9.6, 1.29; 514/1, 1.1; 530/300; 977/904, 927, 928, 929, 930
See application file for complete search history.

(56) References Cited

U.S. PATENT DOCUMENTS

2012/0077958 A1 3/2012 Caravan

FOREIGN PATENT DOCUMENTS

| JP | 3991086 B2 | 10/2007 |
|---|---|---|
| JP | 2010-512369 A | 4/2010 |
| KR | 10-1093549 B1 | 12/2011 |

OTHER PUBLICATIONS

Chopra, "Cy5.5-containing matrix metalloproteinase(MMP) activatable peptide conjugated to glycol chitosan (GC)-coated gold nanoparticles (AuNPs)," *Molecular Imaging and Contrast Agent Database*, pp. 1-3 (Published on Mar. 6, 2012).
Yoon, "Nano X-ray Imaging and Life Science," *Polymer Science and Technology*, vol. 20(3), pp. 232-238 (Published on Jun. 2009).

*Primary Examiner* — D L Jones
(74) *Attorney, Agent, or Firm* — Riverside Law, LLP

(57) ABSTRACT

The present invention relates to a CT contrast agent for detecting a thrombus, comprising fibrin-targeted peptide sequence-conjugated glycol chitosan-gold nanoparticles. The CT contrast agent for detecting a thrombus according to an embodiment of the present invention may allow rapid and repeated acquisition of CT image information related to the size and location of a thrombus in cardio-cerebral vascular thrombosis, and also enables the imaging monitoring of cerebral thrombus.

5 Claims, 4 Drawing Sheets

US 9,717,807 B2

CT CONTRAST MEDIUM FOR DETECTING THROMBUS, COMPRISING FIBRIN-TARGETED PEPTIDE SEQUENCE-CONJUGATED GLYCOL CHITOSAN-GOLD NANOPARTICLES

CROSS-REFERENCE TO RELATED APPLICATIONS

This application is the U.S. national phase application filed under 35 U.S.C. §371 claiming benefit to International Patent Application No. PCT/KR2013/004213, filed on May 13, 2013, which is entitled to priority under 35 U.S.C. §119(a)-(d) to Korea application no. 10-2012-0054614, filed May 23, 2012, each of which application is hereby incorporated herein by reference in its entirety.

TECHNICAL FIELD

The present invention relates to a CT contrast agent for detecting a thrombus, which includes fibrin-targeted peptide sequence-conjugated glycol chitosan-gold nanoparticles.

BACKGROUND ART

Thrombosis in a cardiovascular system, particularly, arterial thrombosis, venous thrombosis, and cardiac thrombosis cause many diseases such as stroke, heart attack, deep vein thrombosis, or a pulmonary embolism. Among others, acute thrombosis causing acute cerebral infarction has recently increased with the development of modern society and has become a major social issue.

Further, from an economic aspect, a total cost resulting from strokes reaches a range of ten billion dollars or more each year globally; for example, there are direct costs related to hospital expenses and nursing costs such as hospital stay, treatment by doctors and health professionals, medicine, home health costs, and other medical goods, and indirect costs such as productivity losses due to disease, productivity losses due to death, or the like.

Many attempts to prevent and treat stroke, which is a major social issue in health care, have been continuously developed for the last 60 years by many researches, and thus, angiography, heart valve prosthesis, computed tomography (CT), transcranial doppler (TCD), and so forth have been studied.

Recently techniques involving an injection of a thrombolytic agent such as a tissue plasminogen activator (tPA) to reduce neurobiological damage have begun to emerge.

In the case of Korea, it is reported that there are about hundred thousand people who have an acute stroke (about 80% of them have cerebral infarction), and approximately 3 to 4% of the patients are treated with tPA. Accordingly, the economic benefits Korea from using tPA are estimated to be about 20 billion won.

According to the NINDS tPA trial, i.e. in case of conventional intravenous thrombolytic treatment, it was determined that a probability that patients will live independently without other people's help is one out of every seven patients; moreover, it turned out to carry problems that patients only within 3 to 6 hours from the symptom onset can be treated.

The problems seem to result from the fact that intravenous thrombolytic therapy has a mild to moderate effect while the side effect of the treatment is not low; about 5 to 10% patients have cerebral hemorrhage, cerebral edema, or the like. Therefore, by increasing the effect of thrombolytic treatments and reducing the side effects, and by increasing the range of treatable patients, post-stroke recovery from initial deficit will be increased. Subsequent humanitarian benefits for patients and their families and consequent national and economic benefits will be great.

Iodine-based contrast agent used as a CT contrast agent could have side effects and toxicity, and these conventional CT contrast agents are not targeted to a specific disease; thus, it can't diagnose a disease unless there is tissue damage and in particular, there is no method of imaging a thrombus which is the cause of a cerebral infarction.

Recently, there have been studies using gold nanoparticles as a CT contrast agent. Since gold has higher molecular weight than iodine, and gold nanoparticles have about 2.65 times higher X-ray absorption coefficient per unit of weight than iodine (based on an X-ray intensity of 100 keV). Thus, gold nanoparticles are highly useful as a CT contrast agent. Moreover, gold nanoparticles are easy to control in terms of the modification of the size and surface characteristics. Furthermore, gold nanoparticles are biocompatible, thus they may well be utilized for developing biomedical techniques. In addition, using such optical properties as suppressing fluorescence would provide advantages in other fields of imaging.

In the monitoring of thrombus, since there is a problem that delayed treatment worsens stroke outcome, CT (particularly non-contrast CT) that allows a more rapid acquisition of brain images compared with MRIs, is widely used as an imaging tool for thrombus monitoring.

However, when non-contrast CT as described above is used, there are many cases that the location or a size of thrombi could not be determined. Thus, the following problems regarding the thrombus monitoring can occur: the determination of individual volume of a thrombolytic agent or the triage of interventional treatment (vs. pharmacologic treatment) is difficult, and thus a pre-determined fixed dose tPA protocol instead of tailored therapy is being used in clinic.

Although there is a method using MRI for non-invasive thrombus imaging, with no sacrifice of experimental animals, quantification is relatively difficult and the cost is relatively high compared with CT; a large size quantitative experiments are difficult to be performed using MR-based thrombus imaging Therefore, there is an urgent need for solving these problems.

DISCLOSURE

Technical Problem

The present invention is directed to providing a CT contrast agent for detecting a thrombus, including fibrin-targeted peptide sequence-conjugated glycol chitosan-gold nanoparticles.

Further, the present invention is directed to providing an imaging-based thrombus monitoring method using the CT contrast agent for detecting a thrombus.

Technical Solution

The present invention provides a CT contrast agent for detecting a thrombus, including fibrin-targeted peptide sequence-conjugated glycol chitosan-gold nanoparticles.

Further, the present invention provides an imaging-based thrombus monitoring method using the CT contrast agent for detecting a thrombus.

Advantageous Effects

The CT contrast agent for detecting a thrombus, including fibrin-targeted peptide sequence-conjugated glycol chitosan-gold nanoparticles according to the embodiment of the present invention can rapidly and repeatedly obtain CT imaging information related to the size and location of a thrombus, and also has an effect of enabling the imaging-based monitoring of cerebral thrombosis.

MODES OF THE INVENTION

Figure 1:
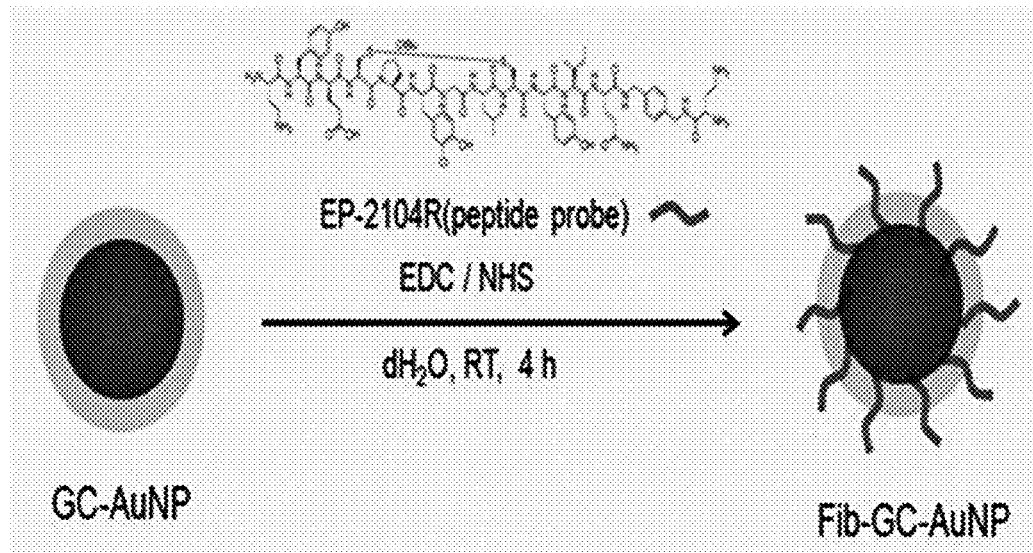
FIG. 1 is a brief view showing a preparation process of fibrin-targeted peptide sequence-conjugated glycol chitosan-gold nanoparticles as an embodiment of the present invention.

The present invention provides a CT contrast agent for detecting a thrombus, including glycol chitosan-gold nanoparticles to which a fibrin-targeted peptide sequence represented by Formula 1 was conjugated.

bus. Since our human body is balanced with various thrombus formation factors and controlling elements, an excessive amount of the thrombus is not formed in a normal human body. However, when the factors involved in thrombus formation control are out of balance, a thrombus may be formed. As causes of the thrombosis, a sluggishness of a blood flow, an excessive coagulation, and damage of a blood vessel are representative, and the three causes contribute separately or together to thrombosis. Various symptoms may be generated according to the location of an organ or a blood vessel in which thrombosis occurred. In the case of arterial thrombosis, ischemic symptoms mainly occur when a peripheral blood flow is insufficient because blood is not supplied well, and in the case of phlebothrombosis, swollen or congestion symptoms mainly occur because blood could reach to a periphery but could not return to the heart. The existence of a thrombus is determined and diagnosed through various examinations such as ultrasonography, CT, MRI, angiography, radioisotope scanning, etc. In the embodiment of the present invention, a CT-based imaging is used to monitor thrombus.

Thrombosis includes cerebral thrombosis, cardiovascular thrombosis, peripheral vascular thrombosis, or the like, but is not limited thereto.

"Cerebral thrombosis" indicates a disease generated by arteriosclerosis due to a thickened cerebral arterial wall complicated with thrombus, which obstructs the flow of blood. Cerebral thrombosis causes an ischemic brain lesion, and is a main cause of encephalomalacia. Although the mechanism of thrombosis associated with arteriosclerosis Formula 1

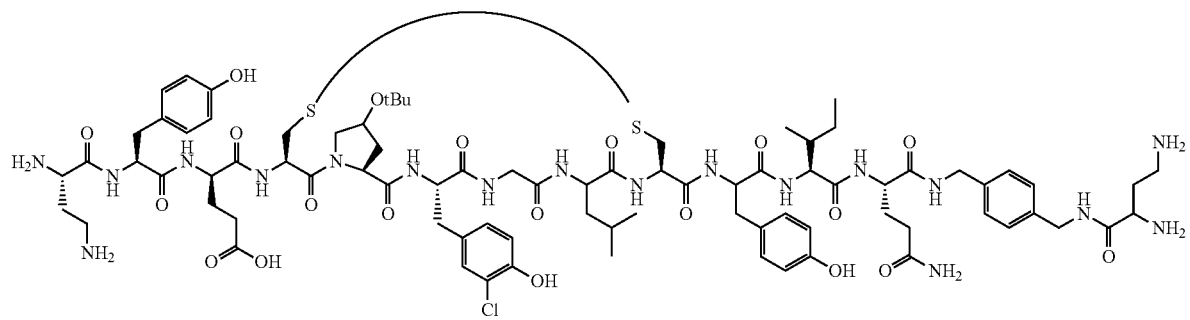

The fibrin-targeted peptide sequence is sequentially composed of tyrosine, D-glutamate, cysteine, hydroxyproline, L-3-chlorotyrosine, glycine, leucine, cysteine, tyrosine, isoleucine, and glutamate.

Further, the present invention provides a CT-based imaging method for thrombus monitoring:

1) a step of injecting glycol chitosan-gold nanoparticles to which a fibrin-targeted peptide sequence represented by Formula 1 was conjugated (a CT contrast agent for detecting a thrombus) to an animal that has thrombosis (but not a human), including.

2) a step of obtaining CT images using micro CT.

Hereinafter, an embodiment of the present invention will be described in detail.

The term "thrombosis" used in the embodiment of the present invention denotes a disease generated due to a "thrombus" which is a blood clot formed inside a blood vessel, also called a thromboembolism, and particularly, denotes a disease of blood vessels obstructed by the thromhas not been identified, it includes hypotension-mediated sluggish blood flow and systemic effects (such as hypercoagulability) as well as an ulcer in a hardened part, edema, and bleeding, or the like. The areas where cerebrovascular changes mostly occur are the branches of the middle cerebral artery, as in cerebral hemorrhage, followed by the anterior cerebral artery and the posterior cerebral artery. People aged 60 years or more or and hypertensives may easily have cerebral thrombosis. There are many cases, in which vascular lesions occurs in body areas other than the brain: for example, myocardiopathy, impalpable arteries of lower limbs, or the like.

The "cardiovascular" or "cardiovascular disease" denotes a disease generated in the heart and main arteries. Heart diseases include congenital heart diseases, which exist at birth and acquired heart diseases that develop during a lifetime. As the structure of the heart could be divided into heart muscle, coronary vessels, valves, and conduction system in charge of the electrical impulse of heart, heart diseases may also be classified depending on the disease locations.

Major cardiovascular diseases occur at the main arteries such as the aorta, pulmonary artery, carotid artery, cerebral artery, renal artery, lower extremity arteries (iliac artery, femoral artery, etc.), or the like, due to obstruction, stretching, or bursting hemorrhage.

The shape and size of gold nanoparticles may be controlled by adjusting the concentration of a gold salt solution and the amount of glycol chitosan, and it is preferable that an average diameter of the gold nanoparticles used in the embodiment of the present invention is in a range of about 18 to 22 nm.

The fibrin-targeted peptide sequence-conjugated glycol chitosan-gold nanoparticles used in the embodiment of the present invention have an excellent performance capable of maintaining stability for 45 days or more.

The fibrin-targeted peptide sequence-conjugated glycol chitosan-gold nanoparticles (0.5 to 1.5 mg/ml) used in the embodiment of the present invention may be injected at an amount of 90 to 110 µl.

The term "computed tomography (CT)" used in the embodiment of the present invention denotes photography in which X-rays, which are radiated to target sections of a human body in various directions and penetrate the target sections, are collected using a detector, and a computer reconstructs an image with respect to an absorption difference of the target sections using a mathematical technique. CT has superior resolution and contrast in separating blood, cerebrospinal fluid, white matter, gray matter, tumor, or the like than a conventional X-ray picture, and may express an absorption difference to the minutest details, thus occupying a prominent part in an image diagnosis field.

The embodiment of the present invention may resolve the problem that conventional contrast agents do not allow the determination of the size or location of a thrombus because the contrast media are blocked by the thrombus, and could visualize acute thrombosis that causes stroke within 5 to 15 minutes, which would lead to the determination of the size of a thrombus in a patient's living body, and thus, may propose a monitoring method tailored to each patient's location and size of the thrombus.

Since the type and amount of a thrombolytic agent could be modified according to the location and size of a thrombus monitored as above, patients may be effectively treated.

Thus, a CT contrast agent for detecting a thrombus according to the embodiment of the present invention allows rapid and repeated acquisition of CT image information related to the size and location of a thrombus in cardiocerebral vascular thrombosis, and also enables imaging-based monitoring of cerebral thrombosis.

In the embodiment of the present invention, an animal excluding a human may include dogs, mice, cats, monkeys, sheep, goats, cows, horses, pigs, or the like, but is not limited thereto.

Exemplary embodiments of the present invention will be described in detail below with reference to the accompanying drawings. The following embodiments are merely examples for explanation of the present invention, and not intended to limit a scope of the present invention.

Example 1. Preparation of Fibrin-Targeted Peptide Sequence-Conjugated Glycol Chitosan-Gold Nanoparticles 1. Preparation of an Aqueous Solution of Glycol Chitosan-Coated Gold Nanoparticles After 300 mg of glycol chitosan (molecular weight of 250,000) was dissolved in 300 ml of water, the aqueous solution was filtered through a filter (pore size: 0.45 µm), and thereby, an aqueous solution of glycol chitosan of which impurities are removed from the filter was prepared.

After a gold salt ($HAuCl_4 \cdot 3H_2O$, 0.03 g) was dissolved in 100 ml of water to prepare a solution at the concentration of 1 mM, the solution was heated to 70° C., and thereby, an aqueous solution of a gold salt was prepared. 300 ml of the aqueous solution of glycol chitosan was mixed with 100 ml of the aqueous solution of the gold salt, the mixed solution was reacted in a stirrer for 24 hours, and thereby, an aqueous solution of gold nanoparticles coated with glycol chitosan was prepared.

2. Conjugation of Glycol Chitosan-Coated Gold Nanoparticles and a Fibrin-Targeted Peptide Sequence.

Glycol chitosan gold nanoparticles and fibrin-targeted peptide (MW 1400 g/mol) were added to dimethyl sulfoxide (DMSO) at a weight ratio of 1:5,000, 1-ethyl-3-(3-dimethylaminopropyl) carbodiimide (EDC; MW 155.24 g/mol) and N-hydroxysuccinimide (NHS; MW 115.09 g/mol) was added thereto at the same ratio to have a final volume of 0.5 ml, and then the mixed solution was stirred for 15 minutes. Then, after the solution was added to the aqueous solution of glycol chitosan-gold nanoparticles prepared in Example 1-1 and reacted for 4 hours, the solution was centrifuged (Micro 17TR) at 9,000 rpm and 24° C. for 45 minutes to remove a supernatant liquid for cleaning, redistributed in $dH_2O$, and thereby, fibrin-targeted peptide sequence-conjugated glycol chitosan-gold nanoparticles were prepared.

A preparation process of fibrin-targeted peptide sequence-conjugated glycol chitosan-gold nanoparticles was briefly illustrated in FIG. 1.

Comparative Example 1. Preparation of Glycol Chitosan-Gold Nanoparticles

After 300 mg of glycol chitosan (molecular weight of 250,000) was dissolved in 300 ml of water, the aqueous solution was filtered through a filter (pore size: 0.45 µm), and thereby, an aqueous solution of glycol chitosan of which impurities are removed from the filter was prepared.

After a gold salt ($HAuCl_4 \cdot 3H_2O$, 0.03 g) was dissolved in 100 ml of water to prepare a solution at a concentration of 1 mM, the solution was heated to 70° C., and thereby, an aqueous solution of a gold salt was prepared. 300 ml of the aqueous solution of glycol chitosan was mixed with 100 ml of the aqueous solution of the gold salt, the mixed solution was reacted in a stirrer for 24 hours, and thereby, an aqueous solution of gold nanoparticles coated with glycol chitosan was prepared.

Comparative Example 2. Preparation of Citrate-Gold Nanoparticles

Citrate-gold nanoparticles were prepared in the same manner as Comparative Example 1 except that a citrate was used instead of glycol chitosan.

Experimental Example 1. Density Measurement of CT Thrombus Image Obtained Using Fibrin-Targeted Peptide Sequence Conjugated-Glycol Chitosan-Gold Nanoparticles A thrombus was prepared by mixing thrombus and the gold nanoparticles prepared in Example 1 and Comparative Examples 1 and 2. After each 5 cm of the thrombus was cleaned and immersed in an EP tube, each thrombus was imaged by using CT to measure its density. The results are shown in FIGS. 2 and 3.

Figure 2:
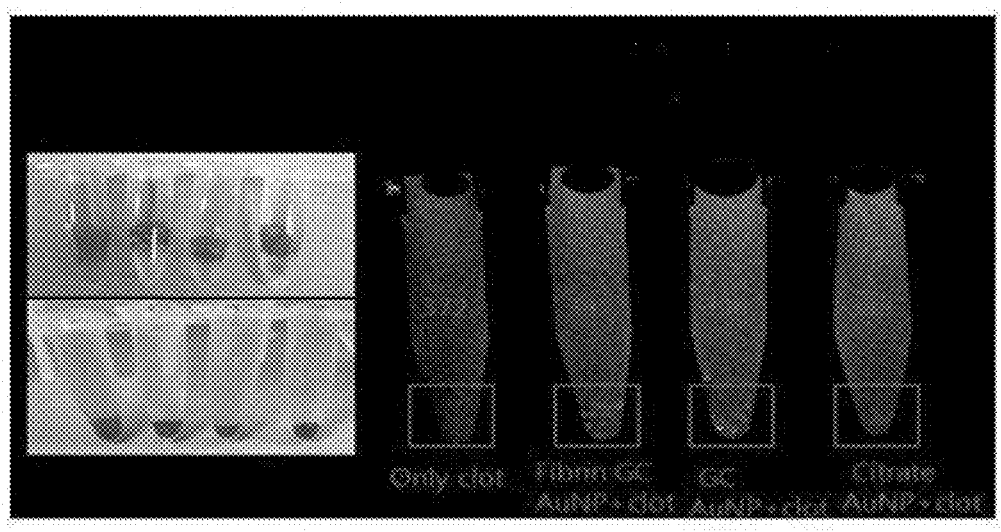
FIG. 2 is a view showing CT images of a thrombus mixed with fibrin-targeted peptide sequence-conjugated glycol chitosan-gold nanoparticles as an embodiment of the present invention.

As shown in FIG. 2, the CT density of the thrombus in the image obtained using fibrin-targeted peptide sequence-conjugated glycol chitosan-gold nanoparticles was higher than that of glycol chitosan-gold nanoparticles or citrate-gold nanoparticles, and the thrombus was more evenly well detected when fibrin-targeted peptide sequence-conjugated glycol chitosan-gold nanoparticles were used.

Figure 3:
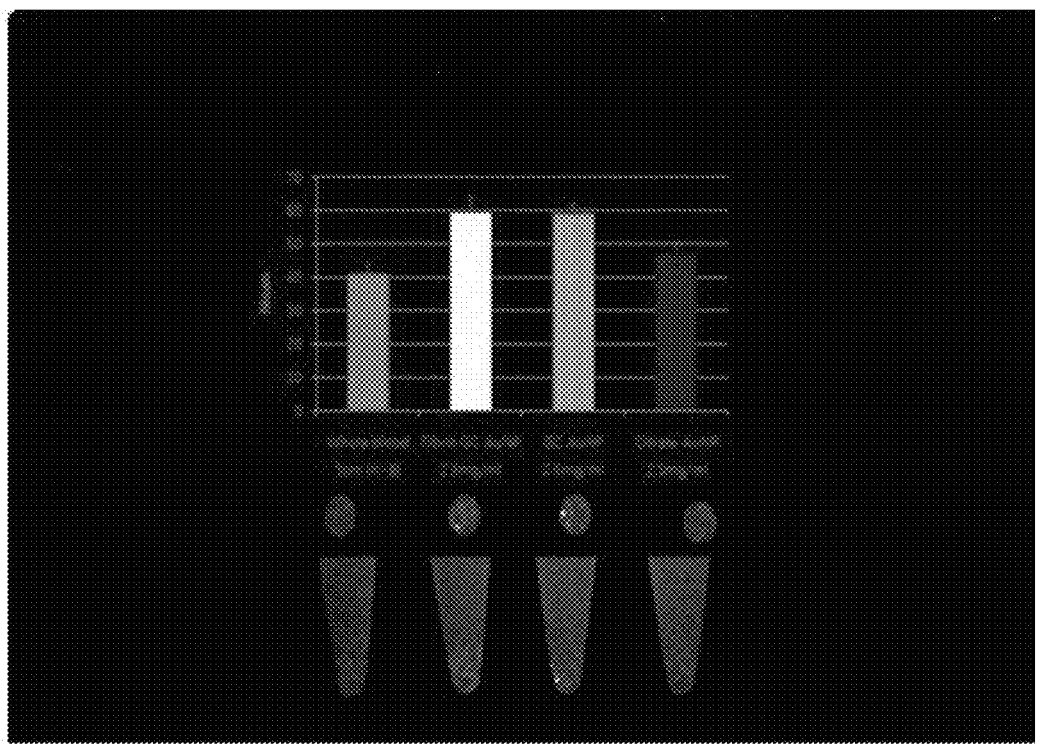
FIG. 3 is a view showing quantified pixel values for the results of FIG. 2.

Further, as shown in FIG. 3, when the result of FIG. 2 was quantified to get pixel values, signal of the thrombus in the CT image obtained by using fibrin-targeted peptide sequence-conjugated glycol chitosan-gold nanoparticles was shown to be relatively stronger.

Experimental Example 2. CT Imaging of Carotid Thrombosis Using Fibrin-Targeted Peptide Sequence-Conjugated Glycol Chitosan-Gold Nanoparticles Mice (C57/BL6) were inhalation-anesthetized with 3% isoflurane and maintained at 37° C. using a homeothermic blanket (Panlab). After mice were put under an operating microscope (Leica, EZ4, 8×) and cut to expose the left common carotid artery, a filter paper (1×1 mm$^2$ or 1×2 mm$^2$) immersed in 10% ferric chloride solution for 5 minutes was put on the carotid artery. Thirty minutes or 120 minutes later after the induction of thrombosis, 100 ul of fibrin-targeted peptide sequence-conjugated glycol chitosan-gold nanoparticles (GC-AuNP) (2.5 mg/ml or 0.25 mg/ml) was injected into the tail vein using a 1 cc syringe. After 5 minutes, images were obtained using micro CT (Nanofocusray, Polaris-G90, parameter: 65 KV, 60 uA, 512×512 reconstruction). The location and size of a thrombus were observed using the obtained images. Here, 3D reconstruction of the DICOM files of the obtained images may be further performed using Lucion software.

Figure 4:
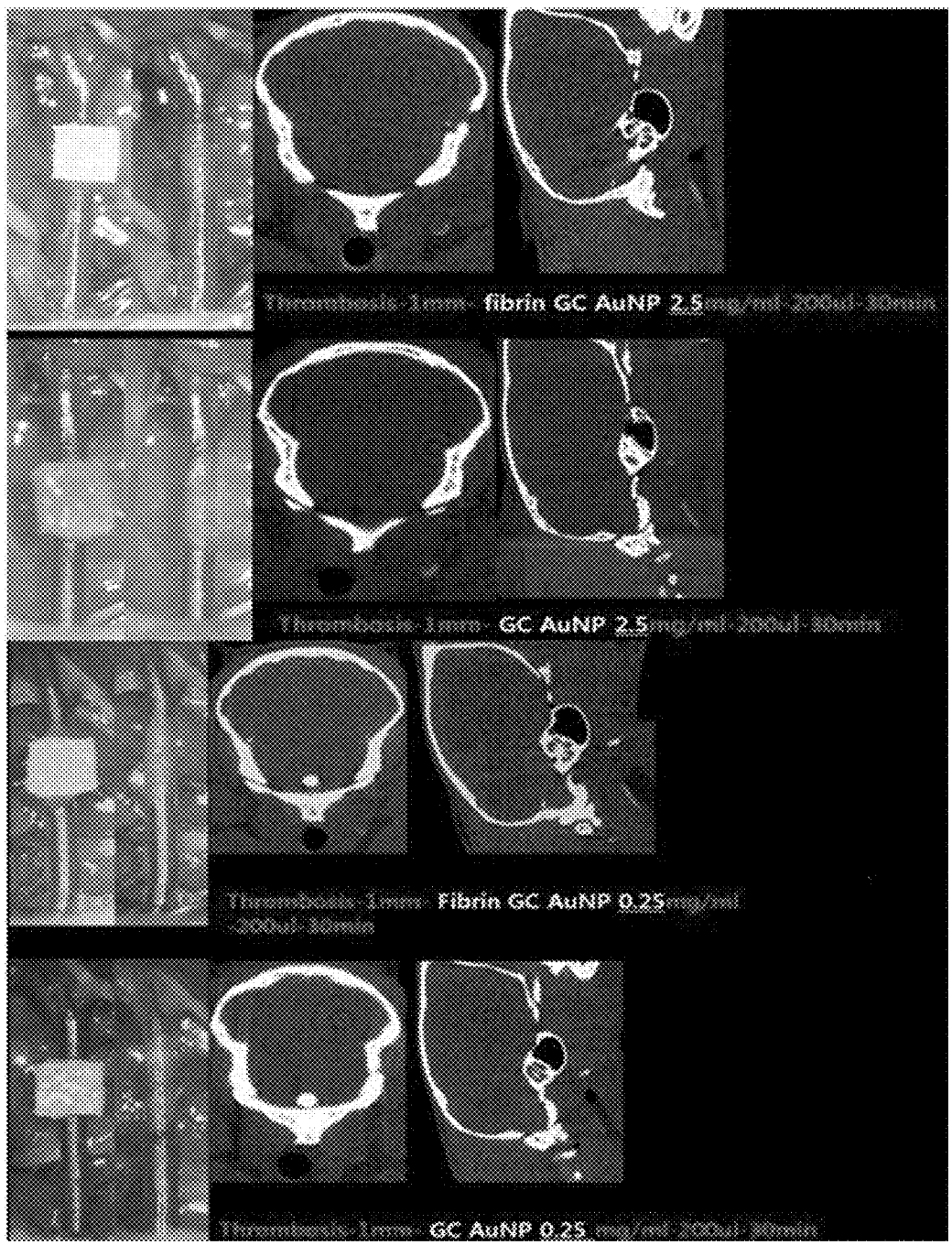
FIG. 4 is a view showing CT images of carotid artery thrombosis, taken using fibrin-targeted peptide sequence-conjugated glycol chitosan-gold nanoparticles (the embodiment of the present invention) as a contrast agent.

The results are shown in FIG. 4.

As shown in FIG. 4, CT-based thrombus images of carotid thrombosis, between the images obtained using 2.5 mg of glycol chitosan-gold nanoparticles and images obtained using 2.5 mg of fibrin-targeted peptide sequence-conjugated glycol chitosan-gold nanoparticles, there seemed to be no difference, but images obtained using 0.25 mg of fibrin-targeted peptide sequence-conjugated-glycol chitosan-gold nanoparticles had stronger thrombus signal than the images obtained 0.25 mg of glycol chitosan gold nanoparticles.

Experimental Example 3. CT Imaging of Cerebral Thrombosis Using Fibrin-Targeted Peptide Sequence-Conjugated-Glycol Chitosan-Gold Nanoparticles CT images of cerebral thrombosis were obtained in the same manner as Experimental Example 2 except that thrombosis was generated in the brain of mice instead of in the left common carotid artery of the mice.

Figure 5:
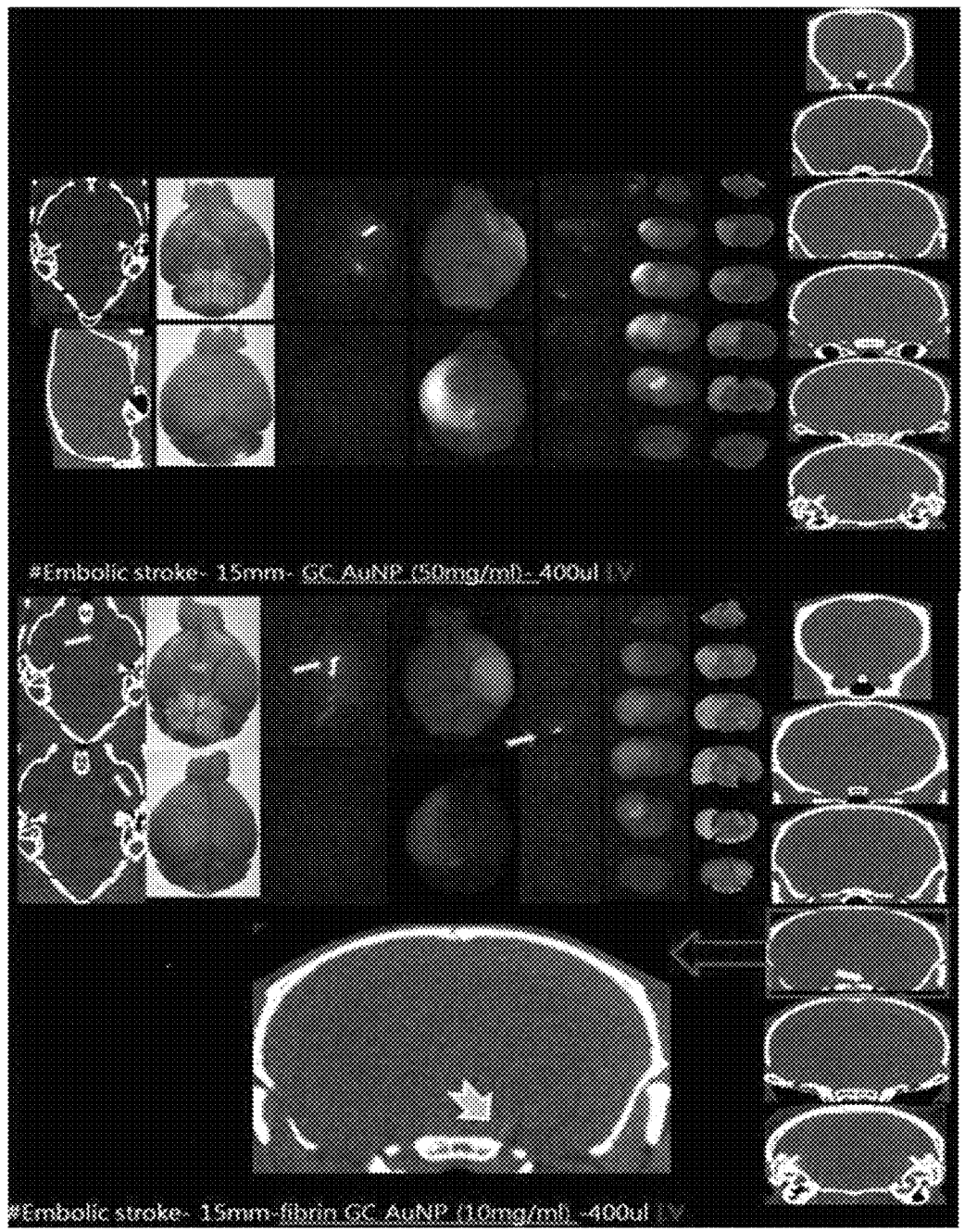
FIG. 5 is a view showing CT images of cerebral thrombosis, taken using fibrin-targeted peptide sequence-conjugated glycol chitosan-gold nanoparticles (the embodiment of the present invention) as a contrast agent.

The results are shown in FIG. 5.

As shown in FIG. 5, CT-based thrombus images of cerebral thrombosis, while the thrombus was not visualized even when 20 mg of glycol chitosan-gold nanoparticles was injected intravenously, when 4 mg of fibrin-targeted peptide sequence-conjugated glycol chitosan-gold nanoparticles was injected, cerebral thrombi could be observed in a living body.

The invention claimed is:

1. A CT contrast agent for detecting a thrombus, comprising a glycol chitosan-gold nanoparticle, to which fibrin-targeted peptide sequences represented by Formula 1 are conjugated;

Formula 1

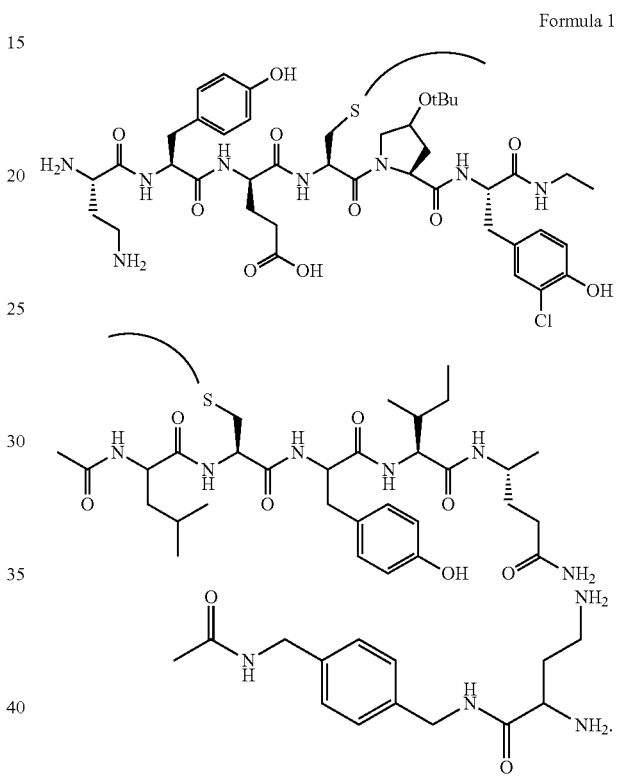

2. A method of thrombus monitoring using CT imaging, comprising:
1) a step of injecting a CT contrast agent for detecting a thrombus, which comprises glycol chitosan-gold nanoparticles to which fibrin-targeted peptide sequences represented by Formula 1 are conjugated, into an animal but not a human, which has thrombosis; and
2) a step of obtaining a CT image using micro CT;

Formula 1

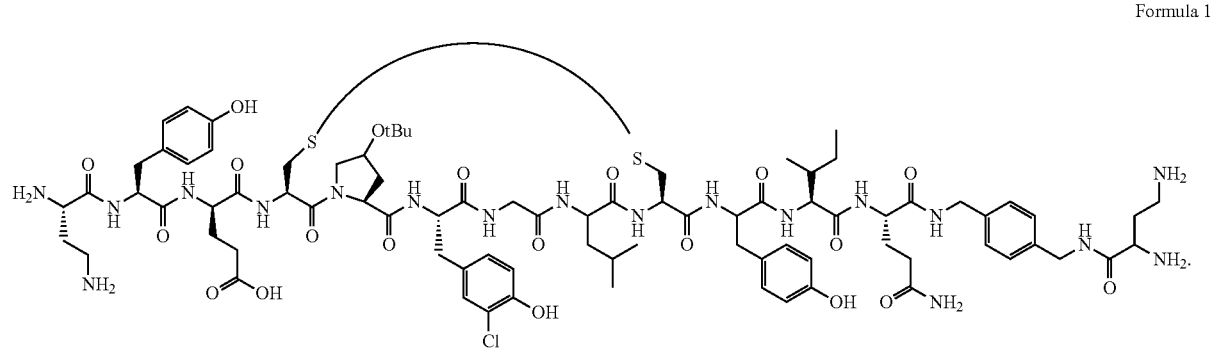

3. The method of claim 2, wherein the animal is one type or more selected from the group consisting of dogs, mice, cats, monkeys, sheep, goats, cows, horses, and pigs.

4. The method of claim 2, wherein the thrombosis is one type or more selected from the group consisting of cerebral thrombosis, cardiovascular thrombosis, and peripheral vascular thrombosis.

5. The method of claim 2, further comprising a step of 3D-reconstruction of the CT image after step 2).

* * * * *